United States Patent
Craig et al.

(10) Patent No.: US 6,552,122 B2
(45) Date of Patent: *Apr. 22, 2003

(54) AQUEOUS EMULSIONS OF AMINE-FUNCTIONALIZED ORGANOPOLYSILOXANES

(75) Inventors: Daniel Horace Craig, Niskayuna, NY (US); Wayne Francis Morgan, Mechanicville, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/785,362

(22) Filed: Feb. 20, 2001

(65) Prior Publication Data

US 2001/0008917 A1 Jul. 19, 2001

Related U.S. Application Data

(62) Division of application No. 09/432,002, filed on Nov. 2, 1999, now Pat. No. 6,214,928.

(51) Int. Cl.$^7$ .................. C08G 77/388; C08G 77/04
(52) U.S. Cl. .................. 524/838; 524/588; 525/902; 525/477; 424/70.12
(58) Field of Search ................. 524/838, 588; 424/70.12; 525/477, 902

(56) References Cited

U.S. PATENT DOCUMENTS

| | | | | |
|---|---|---|---|---|
| 4,535,109 A | * | 8/1985 | Kondo et al. | 524/838 |
| 4,915,938 A | * | 4/1990 | Zawadzki | 424/70.122 |
| 5,045,576 A | * | 9/1991 | Roeck et al. | 524/60 |
| 5,132,443 A | * | 7/1992 | Traver et al. | 424/70.122 |
| 5,726,270 A | * | 3/1998 | Craig | 524/837 |
| 5,807,921 A | * | 9/1998 | Hill et al. | 524/837 |
| 5,856,402 A | * | 1/1999 | Craig et al. | 524/837 |
| 5,900,460 A | * | 5/1999 | Craig | 524/838 |

FOREIGN PATENT DOCUMENTS

EP  0 850 978 A  *  7/1998

OTHER PUBLICATIONS

Hawley's Condensed Chemical Dictionary, Eleventh Edition, Edited by N. Sax & R. Lewis, Sr. (Van Nostrand Reinhold Company, NY, NY, copyright 1987) p. 875, Oct. 1989.*

Milton J. Rosen, Surfactants and Interfacial Phenomena (John Wiley & Sons, NY, NY, copyright 1978) Date received May 1983. p. 224.*

* cited by examiner

*Primary Examiner*—Daniel S. Metzmaier
(74) *Attorney, Agent, or Firm*—Bernadette M. Bennett; Noreen C. Johnson

(57) ABSTRACT

Aqueous emulsions of amine functionalized organopolysiloxane particles useful in personal care applications and methods for making are described. Useful compositions can be made by contacting at elevated temperatures, aqueous emulsions of organopolysiloxane particles having a volume average particle diameter in a range between about 300 nanometers and about 1 micron with an amine functionalized organosilicon source material, such as an aminoorganopolyalkoxysilane or an aminoorganopoly(diorganosiloxane) fluid.

8 Claims, No Drawings

AQUEOUS EMULSIONS OF AMINE-FUNCTIONALIZED ORGANOPOLYSILOXANES

This application is a division of application Ser. No. 09/432,002, filed Nov. 2, 1999 which is hereby incorporated by reference in its entirety, now U.S. Pat. No. 6,214,928.

BACKGROUND OF THE INVENTION

The present invention is directed to stable anionic aqueous emulsions of organopolysiloxane particles having a volume average particle diameter (Dv) of at least about 300 nanometers (nm) and consisting essentially of chemically combined aminoorganosiloxy functional units and diorganosiloxy units. More particularly, the present invention is directed to a method involving the reaction of an aqueous acid catalyzed emulsion of organopolysiloxane particles with an amine functional organosilicon material.

There is shown in U.S. Pat. Nos. 5,726,270, 5,856,402, and 5,900,460 to Craig, semi-continuous methods for making acid catalyzed aqueous dispersions of organopolysiloxanes useful in coating applications, including personal care. For example, in the formulation of a silicone-containing hair shampoo, experience has shown that desirable results can be achieved with aqueous dispersions of organopolysiloxane particles having a volume average particle diameter in the range of at least about 300 nanometers to about 1 micron. It has been found that improvements in hair styling with silicone-containing shampoos can be achieved in particular situations as a result of the "smoothing out" effect. It is speculated that silicones in the form of aqueous dispersions of organopolysiloxane particles having an average diameter of at least about 300 nanometers can more readily coat the surface of the hair shaft.

Experience also has shown that further benefits in coating and in personal care applications can be obtained with aqueous dispersions of organopolysiloxane particles if the dispersed particles are modified with a functional group, such as aminoorgano, epoxy, carboxy, or mercapto. However, previous efforts to functionalize such organopolysiloxane particles during their initial formation from cyclic poly(diorganosiloxane) under semi-continuous conditions, often resulted in functionalized organopolysiloxane particles with a volume average particle diameter less than about 300 nanometers. In particular, although an aqueous emulsion of organopolysiloxane particles having a volume average particle diameter of at least about 300 nanometers can be generated under semi-continuous conditions by the acid catalyzed equilibration of cyclic poly(diorganosiloxane) in the absence of the amine functionalized organosilicon source material, efforts to functionalize the particles during the initial particle formation under semi-continuous conditions in the presence of an amine functionalized organosilicon source material typically results in particles having a volume average particle diameter less than about 300 nanometers.

Further, a procedure for making an acid catalyzed aqueous dispersion of organopolysiloxane particles with aminoorgano functional groups involves working with competing anionic and cationic charges. In addition to adversely affecting particle size, amine functionalization efforts also can impact adversely on emulsion stability and acid-catalyzed polymerization rates. In particular, emulsion instability is favored as a result of the presence of aminoorgano functional groups, and anionic silicone emulsion particles as shown by U.S. Pat. No. 5,045,576. A satisfactory method is therefor needed to make stable aqueous emulsions of amine functionalized organopolysiloxane particles having a volume average particle diameter of at least about 300 nanometers using an acid catalyzed process.

BRIEF SUMMARY OF THE INVENTION

In one embodiment, the present invention is an aqueous emulsion of amine functionalized organopolysiloxane particles useful in personal care applications, and having a volume average particle diameter of at least about 300 nanometers.

In another embodiment, the present invention is a substantially stable aqueous emulsion having in a range between about 5% by weight and about 60% by weight solids, comprising amine functionalized organopolysiloxane particles having a volume average particle diameter of at least about 300 nanometers, said particles consisting essentially of in a range between about 50 mole % and about 99 mole % of diorganosiloxy units, chemically combined with in a range between about 50 mole % and about 1 mole % of (aminoorgano)organosiloxy units.

In still another embodiment, the present invention is a method for making an aqueous emulsion of amine functionalized organopolysiloxane particles useful in personal care applications, and having a total solids content in a range between about 5% by weight and about 60% by weight, comprising effecting reaction at a temperature in a range between about 25° C. and about 110° C., and in the presence of an effective amount of an acid catalyst surfactant, between (A) an aqueous emulsion of organopolysiloxane particles having a volume average particle diameter of at least about 300 nanometers, and (B) an amine functionalized organosilicon source material, wherein there is used in a range between about 1 part and about 50 parts by weight of (B) per 100 parts of (A).

In still another embodiment, the present invention is a method for making a substantially stable aqueous emulsion having in a range between about 5% by weight and about 60% by weight of solids, and comprising amine functionalized organopolysiloxane particles having a volume average particle diameter of at least about 300 nanometers, comprising the steps of:

(1) providing an aqueous emulsion comprising in a range between about 1% by weight and about 50% by weight organopolysiloxane particles having a volume average particle diameter of at least about 300 nanometers, by either, (a) equilibrating under semi-continuous conditions at a temperature in a range between about 25° C. and about 110° C., an aqueous mixture comprising cyclic poly(diorganosiloxane) and an effective amount of an acid catalyst surfactant to form an aqueous emulsion of organopolysiloxane particles having a volume average particle diameter of at least about 300 nanometers, or (b) employing an aqueous emulsion of preformed organopolysiloxane emulsion seeds having a volume average particle diameter of at least about 300 nanometers; and (2) effecting reaction between the organopolysiloxane particles or seeds in the aqueous emulsion of (1), and an amine functionalized organosilicon source material in a range between about 1 part and about 50 parts by weight per 100 parts of such organopolysiloxane particles or seeds.

DETAILED DESCRIPTION OF THE INVENTION

Within the context of the present invention "substantially stable aqueous emulsion" means an emulsion in which the dispersed particles do not appreciably agglomerate during the typical shelf-life of the emulsion. In one of its embodiments "semi-continuous" refers to a process for functionalizing organopolysiloxane particles which employs organopolysiloxane particle seeds prepared in a separate step. In other embodiments, "semi-continuous" refers to a reaction which does not need to be stopped in order to add more reactants.

The present invention is based on the discovery that effective aminoorgano functionalization of dispersed organopolysiloxane particles having a volume average particle diameter of at least about 300 nanometers can be achieved by direct treatment of an acid catalyzed aqueous dispersion of said particles with an amine functionalized organosilicon source material in the form of an aminoorgano functionalized organosilicon member selected from the group consisting of an alkoxysilane, a cyclic poly(diorganosiloxane), and a poly(diorganosiloxane) fluid. Surprisingly, the volume average particle diameter of the resulting aminoorgano functionalized particles is found to be substantially the same as the volume average particle diameter of the starting unfunctionalized organopolysiloxane particles.

In one embodiment, a substantially stable aqueous emulsion of functionalized organopolysiloxane particles with the desired size range is produced by a two-staged, acid-catalyzed semi-continuous/semi-continuous or semi-continuous/batch process whereby the particle size is substantially maintained from the first stage and functionalization occurs in a second stage through equilibration into the particles of an amine functionalized organosilicon source material, particularly an aminoorgano functionalized alkoxy silane, cyclic poly(diorganosiloxane), or poly(diorganosiloxane) fluid. "Substantially maintained" as used herein refers to a volume average particle size of organopolysiloxane particles which changes less than about 50%, preferably less than about 20%, and most preferably less than about 10%. Often, a semi-continuous process is utilized in the first stage wherein, for example, a cyclic poly(diorganosiloxane), acid catalyst surfactant, and water are added to a preheated reactor, either as separate feeds or in various combinations with each other, or as a pre-emulsified mixture containing water and optionally additional surfactant over some specified time period. The reaction mixture may be heated for a period of time after addition of precursor to ensure formation of organopolysiloxane particles in the desired size range. Upon completion of the first stage, the reaction mixture may be cooled to any desired temperature, for example to about room temperature, or maintained at reaction temperature. The amine functionalized organosilicon source material may be added, either semi-continuously or batchwise, at which point the reactor may be heated to a desired reaction temperature or simply maintained at a desired reaction temperature for a period of time to ensure equilibration of functionalized species into the particles. The length of time between stages may be of any convenient duration provided a particle size in the desired range is substantially achieved in the first stage and adequate functionality incorporation is achieved in the second stage.

In another embodiment, a substantially stable aqueous emulsion of functionalized organopolysiloxane particles with the desired size range is produced by post-functionalization of a pre-existing, pre-synthesized organopolysiloxane emulsion comprising particles with volume average particle diameter of at least about 300 nanometers. Post-functionalization using amine functionalized organosilicon source material may be performed essentially as described above. The synthesis of the pre-existing emulsion can occur at any point prior to the functionalization step, including a separate emulsion manufacturing step.

Aqueous emulsions of organopolysiloxane particles used in the practice of the present invention can be employed as preformed organopolysiloxane particles or "seeds". Said particles typically have a volume average particle diameter ($D_v$) of at least about 300 nanometers, and preferably in a range between about 300 nanometers and about 1 micron. Alternatively, the initial volume average diameter of said particles may be less than about 300 nanometers and is increased to greater than about 300 nanometers before functionalization, for example through equilibration with cyclic poly(diorganosiloxane) in the presence of catalyst.

Another source of the organopolysiloxane particles is by the equilibration of at least one cyclic poly(diorganosiloxane). Accordingly, an aqueous mixture having in a range between about 5% by weight and about 60% by weight of cyclic poly(diorganosiloxane) can be agitated and equilibrated in the presence of an acid catalyst surfactant at temperatures in a range between about 25° C. and about 110° C. Equilibration of the cyclic poly(diorganosiloxane) can be conducted in a semi-continuous manner to form particles comprising poly(diorganosiloxane) structural units and having a volume average particle diameter of at least about 300 nanometers, and preferably in a range between about 300 nanometers and about 1 micron.

Cyclic (polydiorganosiloxane)s included in the practice of the invention, are for example, one or more members selected from a $C_{3-8}$ cyclic diorganosiloxane, and most preferably a $C_{3-4}$ cyclic poly(dimethylsiloxane), such as hexamethyltrisiloxane and octamethylcyclotetrasiloxane, or "tetramer". However, other $C_{1-6}$ organo radicals can be present in addition to or in place of methyl, such as ethyl, propyl, butyl and phenyl.

Acid catalyst surfactants include, for example, surface-active sulfonic acids, which can be substituted with alkyl, alkaryl, or aryl radicals. Examples of mixtures of surface-active sulfonic acid salts with strong mineral acids, and combinations thereof are disclosed in U.S. Pat. No. 3,294,725, also can be used. A particularly preferred acid catalyst surfactant is dodecylbenzenesulfonic acid. An effective amount of the acid catalyst surfactant is in a range between about 0.25% by weight and about 5% by weight of acid catalyst surfactant based on the weight of cyclic poly(diorganosiloxane) initially present in the aqueous mixture. Preferred weight ratios of cyclic poly(diorganosiloxane) to acid catalyst surfactant to water can vary in a range between about 70:1:29 and about 75:5:20.

Among the amine functionalized organosilicon source materials which can be used in the practice of the invention, there are included aminoorganopolyalkoxysilanes, such as gamma-aminopropyltrimethoxysilane and gamma-aminopropyltriethoxysilane.

Aminoorgano-substituted organopolysiloxanes, such as amine functionalized poly(diorganosiloxane) fluids, also can be used as amine functionalized organosilicon source materials. These amine source materials can have a viscosity in a range between about 100 centipoise and about 100,000 centipoise at 25° C., and consist essentially of chemically combined aminoalkylorganosiloxy units and diorganosiloxy units, wherein there can be present in a range between about 1 mole % and about 99 mole % of aminoalkylorganosiloxy units, such as aminopropylmethylsiloxy units, based on the total moles of aminoalkylorganosiloxy units and diorganosiloxy units, such as dimethylsiloxy units.

The amount of amine functionalized organosilicon source material used to functionalize organopolysiloxane particles is by weight in a range between about 1 part and about 50 parts, and preferably in a range between about 1 and about 10 parts, per 100 parts of organopolysiloxane particles. Reaction between organopolysiloxane particles and amine functionalized organosilicon source materials can be effected at temperatures in a range between about 25° C. and about 110° C. Depending upon such factors as the identity of the source material, it may be preferred to add the amine functionalized organosilicon source material to existing organopolysiloxane particles at temperatures in a range between about room temperature and about 90° C., and preferably at temperatures in a range between about room temperature and about 40° C. followed by heating the resulting aqueous mixture to minimize premature hydrolysis of alkoxysilicon groups which may result in unwanted coagulum (heterogeneous polysiloxane product) and lower product yield. The final product emulsion typically has in a range between about 5% by weight and about 60% by weight and preferably in a range between about 30% by weight and about 60% by weight solids level.

In order that those skilled in the art will be better able to practice the present invention, the following examples are given by way of illustration, and not by way of limitation. In these examples, all parts which are referenced are by weight unless otherwise indicated.

EXAMPLE 1

An aqueous emulsion of poly(dimethylsiloxane) seeds was prepared by initially heating to 85° C. under continuous agitation for 125 minutes, a mixture of 166 grams of water and 48 grams of a pre-emulsified mixture. The pre-emulsified mixture consisted of 298 grams of octamethylcyclotetrasiloxane, 4.5 grams of dodecylbenzenesulfonic acid, and 110 grams of water. The remainder of the pre-emulsified mixture was then added over 85 minutes. The mixture was maintained at 85° C. for an additional 90 minutes, then cooled to room temperature. Based on method of preparation and the employment of a Nicomp 370 Submicron Particle Sizer instrument, applying a Gaussian analysis protocol, there was obtained an aqueous emulsion of poly(dimethylsiloxane) particles having volume average particle diameter of 431 nanometers.

There was added to the above aqueous emulsion with stirring 4.8 grams of SF1708 (a product of GE Silicones, Waterford, N.Y.), which is a trimethylsiloxy-terminated, amino-substituted methylpolysiloxane fluid consisting essentially of dimethylsiloxy units and (aminopropyl) methylsiloxy units having a viscosity of 2000 centipoise at 25° C., and an amine content of about 0.8 milliequivalents base per gram. The resulting mixture was heated to 85° C. and maintained at that temperature for 270 minutes. The mixture was then cooled to room temperature. Based on method of preparation, and infrared (IR) spectral analysis, there was obtained an aqueous emulsion of aminopropyl functionalized poly(dimethylsiloxane) particles.

Utilizing a CEM Labwave 9000 gravimetric microwave drier with 20 minute heat times and at full microwave output, the emulsion was found to have 45.4% total solids by weight. The volume average particle diameter of the particles in the amino functionalized poly(dimethylsiloxane) emulsion was found to be substantially unchanged as compared to the original aqueous emulsion free of amino functionalization. The amino functionalized poly(dimethylsiloxane) emulsion was found to be stable and compatible with other anionic materials, and can be used in applications such as coatings and personal care.

CONTROL EXAMPLE 1

The following control example shows that when the amine functionalized organosilicon source material is introduced into the reaction mixture either prior to or during the initial formation of the aqueous emulsion of polymerized organopolysiloxane seeds, an amino functionalized poly(dimethylsiloxane) emulsion may result which has volume average particle diameter less than about 300 nanometers.

A mixture of 100 grams of water, 3.2 grams of dodecylbenzenesulfonic acid, 321 grams of octamethylcyclotetrasiloxane, and 4.8 grams of SF1708 was added to a reactor containing 150 grams of water at 86° C. over a period of 310 minutes. The mixture was diluted with 200 grams of water to lower the reaction mixture viscosity, and then maintained for an additional five hours at 86° C., and cooled to room temperature. There was obtained an emulsion of poly(dimethylsiloxane)-containing particles having a volume average particle diameter of 121 nanometers and a total solids level of 38% by weight.

EXAMPLE 2

While 150 grams of water at 86° C. was being agitated in a reactor, there was added over a period of 345 minutes a pre-emulsified mixture of 100 grams of water, 3.2 grams of dodecylbenzenesulfonic acid, and 319 grams of octamethylcyclotetrasiloxane. After completion of the emulsion addition, the resulting reaction mixture was heated for an additional 30 minutes and then cooled rapidly. Based on method of preparation, there was obtained an aqueous emulsion of poly(dimethylsiloxane) seeds having a volume average particle diameter of 935 nm.

The above emulsion was then heated to 38° C., and 4.2 grams of aminosilicone fluid SF1708 was thereafter added batchwise with stirring. The resulting mixture was then heated to 86° C. and maintained at that temperature for 6 hours and cooled to ambient temperature. Based on method of preparation and use of analytical procedures shown in Example 1, there was obtained an aqueous emulsion having 48.1% by weight total solids, of amine functionalized organopolysiloxane particles having volume average diameter of 953 nanometers. The silicone emulsion was also free of coagulum, and stable and compatible with other anionic materials; it can be used in applications such as coatings and personal care.

EXAMPLE 3

There was added batch-wise with constant stirring at 22° C. an aqueous mixture of 9.2 grams of gamma-aminopropyltriethoxysilane and 19.1 grams of dodecylbenzenesulfonic acid to 620 grams of a preformed poly(dimethylsiloxane) emulsion having a total weight % solids of 50.7, and a volume average particle diameter of 731 nanometers. The resulting reaction mixture was heated to 50° C. for 2.5 hours and cooled to room temperature. Based on method of preparation and analytical procedures shown in example 1, there was obtained an aqueous emulsion of amine functionalized organopolysiloxane particles having a volume average particle diameter of 803 nanometers and a total weight % solids of 51.4%. The aqueous emulsion of amine functionalized organopolysiloxane particles is useful in personal care applications.

EXAMPLE 4

A mixture of 300 grams of a preexisting poly(dimethylsiloxane) emulsion (45% solids level; volume average particle diameter of 156 nanometers) was agitated and heated at 85° C. There was added to the reactor over 195 minutes a pre-emulsified mixture of 210 grams octamethylcyclotetrasiloxane, 3.12 grams of dodecylbenzenesulfonic acid and 208 grams water. Additional water (60 grams) was added and the reaction mixture was maintained at 85° C. for an additional 90 minutes, then cooled to room temperature. An aminosilicone fluid SF1708 (4.2 grams) was thereafter added to the reaction mixture with stirring. The resulting reaction mixture was heated at 85° C. for 300 minutes and cooled to room temperature. Based on method of preparation and analytical procedures shown in Example 1, there was obtained an aqueous emulsion of amine functionalized organopolysiloxane particles having a volume average particle diameter of 311 nanometers and a total weight % solids of 40.8%. The aqueous emulsion of amine functionalized organopolysiloxane particles is useful in personal care applications.

Although the above examples are directed to only a few of the very many variables to which the present invention is directed, it should be understood that the present invention is directed to a much broader variety of substantially stable aqueous emulsions of amine functionalized organopolysiloxane particles having a volume average particle diameter in a range between about 300 nanometers and about 1 micron, and methods for making such materials.

What is claimed:

1. An aqueous emulsion of amine functionalized organopolysiloxane particles having a volume average particle diameter of at least about 300 nanometers;

wherein the amine functionalized organopolysiloxane particles are derived from the reaction between organopolysiloxane particles having a volume average particle diameter of at least about 300 nanometers and an aminoorganopolysiloxane; and wherein the volume average particle diameter of the amine functionalized organopolysiloxane particles is substantially maintained upon functionalization.

2. The aqueous emulsion in accordance with claim 1, wherein the aqueous emulsion consists essentially of chemically combined dimethylsiloxy units and (aminopropyl)methylsiloxy units.

3. The aqueous emulsion in accordance with claim 1, which is useful in personal care applications.

4. A substantially stable aqueous emulsion having solids in a range of between about 5% by weight and about 60% by weight, comprising dispersed amine functionalized organopolysiloxane particles that have a volume average particle diameter of at least about 300 nanometers, said particles consisting essentially of diorganosiloxy units in the range between about 50 mole % and about 99 mole % chemically combined with (aminoorgano)organosiloxy units in a range between about 50 mole % and about 1 mole %;

wherein the amine functionalized organopolysiloxane particles are derived from the reaction between organopolysiloxane particles having a volume average particle diameter of at least about 300 nanometers and an aminoorganopolysiloxane; and wherein the volume average particle diameter of the amine functionalized organopolysiloxane particles is substantially maintained upon functionalization.

5. The substantially stable aqueous emulsion in accordance with claim 4, wherein the aminoorganopolyalkoxysilane comprises gamma-aminopropyltriethoxysilane.

6. The substantially stable aqueous emulsion in accordance with claim 4, which is useful in personal care applications.

7. A substantially stable aqueous emulsion having solids in a range of between about 5% by weight and about 60% by weight, comprising dispersed amine functionalized organopolysiloxane particles that have a volume average particle diameter of at least about 300 nanometers, said particles consisting essentially of diorganosiloxy units in the range between about 50 mole % and about 99 mole % chemically combined with (aminoorgano)organosiloxy units in a range between about 50 mole % and about 1 mole %;

wherein the amine functionalized organopolysiloxane particles are derived from the reaction between organopolysiloxane particles having a volume average particle diameter of at least about 300 nanometers and an amine functionalized poly(diorganopolysiloxane) fluid; and wherein the volume average particle diameter of the amine functionalized organopolysiloxane particles is substantially maintained upon functionalization.

8. An aqueous emulsion of amine functionalized organopolysiloxane particles having a volume average particle diameter of at least about 300 nanometers;

wherein the amine functionalized organopolysiloxane particles are derived from the reaction between organopolysiloxane particles having a volume average particle diameter of at least about 300 nanometers and an amine functionalized poly(diorganopolysiloxane) fluid; and wherein the volume average particle diameter of the amine functionalized organopolysiloxane particles is substantially maintained upon functionalization.

* * * * *